US010166387B2

(12) United States Patent
Bergelin et al.

(10) Patent No.: US 10,166,387 B2
(45) Date of Patent: Jan. 1, 2019

(54) ARRANGEMENT FOR FACILITATING WOUND HEALING, A METHOD FOR MEASURING WOUND HEALING AND A WOUND DRESSING

(71) Applicants: Åbo Akademi, Turku (FI); Tampereen teknillinen yliopisto, Tampere (FI)

(72) Inventors: Mikael Bergelin, Turku (FI); Jan-Erik Eriksson, Turku (FI); Max Johansson, Turku (FI); Chunlin Xu, Turku (FI); Ann-Sofie Leppänen, Turku (FI); Stefan Willför, Turku (FI); Simo Köppä, Tampere (FI); Atte Kekonen, Tampere (FI); Heimo O. Ylänen, Tampere (FI); Jari Viik, Tampere (FI); Jari Hyttinen, Tampere (FI)

(73) Assignee: CutoSense Oy, Turku (FI)

( * ) Notice: Subject to any disclaimer, the term of this patent is extended or adjusted under 35 U.S.C. 154(b) by 372 days.

(21) Appl. No.: 14/893,084

(22) PCT Filed: May 21, 2014

(86) PCT No.: PCT/FI2014/050388
§ 371 (c)(1),
(2) Date: Nov. 23, 2015

(87) PCT Pub. No.: WO2014/188070
PCT Pub. Date: Nov. 27, 2014

(65) Prior Publication Data
US 2016/0101282 A1    Apr. 14, 2016

(30) Foreign Application Priority Data

May 23, 2013 (FI) ..................... 20135557

(51) Int. Cl.
*A61N 1/20* (2006.01)
*A61N 1/04* (2006.01)
(Continued)

(52) U.S. Cl.
CPC .............. *A61N 1/205* (2013.01); *A61B 5/053* (2013.01); *A61B 5/0531* (2013.01); *A61B 5/445* (2013.01);
(Continued)

(58) Field of Classification Search
CPC .... A61N 1/205; A61N 1/0468; A61N 1/0476; A61N 1/0484; A61N 1/0496;
(Continued)

(56) References Cited

U.S. PATENT DOCUMENTS

2006/0182788 A1* 8/2006 Singh .................. A61K 9/7061
424/448
2006/0270942 A1* 11/2006 McAdams ........... A61B 5/0531
600/547

(Continued)

FOREIGN PATENT DOCUMENTS

WO    WO 2004049937 A1    6/2004
WO    WO 2006081497 A2    8/2006
(Continued)

*Primary Examiner* — Michael Carey
(74) *Attorney, Agent, or Firm* — Seppo Laine Oy

(57) ABSTRACT

A wound dressing according to the present invention comprises at least two impedance reference electrodes, a frame like counter-electrode and stimulation electrodes in a form of an array; and a bioadhesive affinity layer surrounding the stimulation electrodes; said wound dressing being suited for applying on top of the wound so that the stimulation electrode array is on the wound area, and that the at least two impedance reference electrodes and the frame like counter-electrode are suited for placing in contact with the healthy skin surrounding the wound area; which electrodes, are (Continued)

suited for applying LIDC type electrical stimulation current to the wound area and for bioimpedance measurement. The wound dressing according to the present invention provide a continuous, non-invasive and objective solution for monitoring chronic wound healing without disturbing the delicate healing process.

20 Claims, 4 Drawing Sheets

(51) Int. Cl.
  *A61B 5/053* (2006.01)
  *A61B 5/00* (2006.01)
  *A61N 1/36* (2006.01)
  *A61F 13/02* (2006.01)

(52) U.S. Cl.
  CPC ........ *A61B 5/4848* (2013.01); *A61F 13/0253* (2013.01); *A61N 1/0468* (2013.01); *A61N 1/0476* (2013.01); *A61N 1/0484* (2013.01); *A61N 1/0496* (2013.01); *A61N 1/36014* (2013.01)

(58) Field of Classification Search
  CPC .. A61N 1/36014; A61B 5/053; A61B 5/0531; A61B 5/445; A61B 5/4848; A61F 13/0253
  USPC .................................. 607/50; 600/300, 301
  See application file for complete search history.

(56) References Cited

U.S. PATENT DOCUMENTS

| | | | |
|---|---|---|---|
| 2008/0103550 A1 | 5/2008 | Wenzel et al. | |
| 2011/0015697 A1* | 1/2011 | McAdams | A61B 5/445 607/50 |

FOREIGN PATENT DOCUMENTS

| | | |
|---|---|---|
| WO | WO 2008013936 A1 | 1/2008 |
| WO | WO 2009092616 A1 | 7/2009 |
| WO | WO 2009144615 A1 | 12/2009 |
| WO | WO 2011004165 A1 | 1/2011 |

* cited by examiner

ARRANGEMENT FOR FACILITATING WOUND HEALING, A METHOD FOR MEASURING WOUND HEALING AND A WOUND DRESSING

FIELD OF THE INVENTION

The present invention relates to the field of electrotherapy and measuring by means of electric currents for diagnostic purposes, and more particularly to an electrode arrangement for facilitating wound healing, a method for measuring wound healing and a wound dressing having an electrode arrangement.

BACKGROUND OF THE INVENTION

Wounds such as e.g. chronic wounds and ulcers affect nearly 1% of population and up to 10% of institutionalized patients. By the year 2030, 366 million people worldwide are estimated to suffer from diabetes further increasing the prevalence of chronic wounds and ulcers.

Aging population in the western world and increase in the prevalence of various diseases exposing to chronic wounds, such as diabetes and vascular diseases, have made it ever more important to develop novel therapeutic methods and further improve the existing therapeutic methods for non-healing ulcers. Social problems for an individual patient are enormous and the financial burden to the healthcare system is huge due to costly treatment of chronic wounds and the related indirect costs. To further underline the prevalent problem of chronic wounds and ulcers, in addition to increased mortality, approximately 80% of leg amputations are due to chronic vascular ulcers.

Lower extremity wounds of venous origin are commonly riddled with peripheral edema. This is due to vascular insufficiency; incompetence and dysfunction of veins and valves to transport blood in a normal way. This results in accumulation of highly conductive fluid into the interstitial space of the affected limb.

Edema prevents appropriate transport of oxygen and nutrients, which is essential for proper wound healing to occur. Edema also adds the mechanical stress in the wound site and disturbs waste removal from the wound area. A commonly used method to ease edema is compression therapy. Compression stockings are used for improving healing of chronic wounds of vascular etiology.

In summary, conventional treatment of chronic wounds and ulcers has so far been mainly passive; firstly to remove or control the impediments for healing and secondly to cover the wound area with an occlusive dressing to allow nature to take its course.

An important finding in the wound care practices was that a moist environment is beneficial to the non-healing wound and that the occlusive dressings do not increase the risk for infection. This may partly relate to the improved ion transport and improved function of endogenous electric fields. Therefore, an ideal dressing for a chronic ulcer would provide a moist environment, absorb exudates, prevent the maceration of surrounding tissue and would be long term and cost effective. For wounds and ulcers that fail to heal, the treatment in the end often leads to surgical debridement under anaesthesia.

Recent studies suggest that endogenous electrical fields generated immediately after skin break may work as an initiating force for wound healing. This is due to instant collapse of transepithelial potential (TEP) in the wound area and resulting short circuit and flow of ionic current. As the wound heals the integrity of skin is gradually regained and eventually TEP is resumed.

Therefore, in order to improve the healing rate, a therapeutic approach which utilizes electrical stimulation of the wound via application of direct current should be beneficial. In a typical electrical stimulation of the wound low current and low voltage direct current is applied to the surface of the wound in order to stimulate the healing of the wound.

The electrical stimulation of the wound has been found to affect the biological healing of the wound in the inflammation phase of the wound, in the proliferation phase of the wound and in the epithelisation phase of the wound. In the inflammation phase of the wound the electrical stimulation of the wound initiates the wound healing process, increases the blood circulation, promotes phagocytosis, improves tissue oxygen intake, reduces edema, stimulates fibroblasts and epithelial cells, stimulates DNA synthesis, calms the infection and dissolves the necrotic tissue. In the proliferation phase of the wound the electrical stimulation of the wound stimulates fibroblasts and epithelial cells, stimulates DNA synthesis and protein synthesis, adenosine triphosphate (ATP) formation, enhances membrane transport and stimulates the diminishing of the wound. In the epithelisation phase of the wound the electrical stimulation of the wound stimulates the reformation and the migration of the epithelial cells and leads to softer and thinner skin, and improved scarring. Higher quality scarring is an important factor in decreasing the high recurring tendency of a chronic wound.

Vascularization plays an important role in soft tissue healing, and hence enhancing angiogenesis to ensure sufficient blood flow in the newly formed epithelial layer will support the healing process. Vascular endothelial growth factor (VEGF) has been successfully used in preclinical ischaemic tissue models to enhance and promote the development of collateral blood vessels. Also, dissolution of certain bioactive glass compositions have been shown to stimulate release of angiogenetic growth factors resulting in an increase in tubule branching and formation of complex networks of interconnected tubules. Soluble products of these bioactive glasses induce endothelial cell proliferation and up-regulation of VEGF production, which indicate that these glasses possess a proangiogenic potential. Significantly enhanced mitogenic stimulation of endothelial cells with an additive effect with VEGF release has also been observed in the presence of a BAG coating.

It has been shown that the applying of electrical stimulation in the form of low intensity direct current (LIDC) to the wound has caused the wound to heal drastically faster and at a wider area. The faster healing of the chronic wounds and ulcers brings substantial savings both in terms of financial costs and human suffering. Chronic wounds are a cause for disability, pain, emotional and social problems for the patients. Chronic wounds are associated with prolonged hospitalizations and considerable morbidity. These wounds, also known as ulcers, represent a major burden for the healthcare system affecting a large population of patients. Chronic wounds persist for months or even years representing medical, social, and economic problems for individuals and the society.

There are some prior art accelerating wound healing products in the market available as consumer products. However, the functionality of these prior art wound healing products is very limited as their principle of operation is based on a large number of independent miniature galvanic cells that are in contact with the wound area. Although this allows for easy adjustment of dressing size, the lack of possibility for controlling the current-flow, both in terms of magnitude and direction, is expected to diminish the effect of this therapy. The problem is that the stimulus current generated by this type of prior art electrode array does not penetrate into the actual wound tissue, but rather mainly flows along the wound surface which severely limits the accelerating effect on the healing process.

Furthermore, one major problem in wound care is associated with monitoring of the healing process. Today, the assessment of progress of chronic wound healing is generally based on visual investigation by photographing and monitoring the size and the colour of the wound. Visual assessment is always influenced by a certain degree of subjectivity. Sometimes ultrasound is used for imaging the structure of the wound; also laboratory tests of exudate samples or biopsied tissue are done. These methods are fairly laborious and cannot be applied for daily assessment of wound healing. All these methods require disturbing the wound by removal of the wound dressing and visual inspection of the wound area to assess the onset of formation of granulation tissue and to ensure that the wound is not becoming infected.

There are some prior art wound monitoring sensors available, e.g. array sensors which take the form of patterns on insulating material. However, these prior art wound monitoring sensors may typically use materials that interfere with or irritate the wound, occlude the wound and can cause skin maceration. Also, some of the prior art wound monitoring sensors adhere to the wound, which can result in wound damage when they are removed. Furthermore, some of the prior art wound monitoring sensors also interfere with the healing of the wound by interfering with moisture control, whilst some only have a limited lifetime in a wound environment.

As the bioimpedance measurement utilizes low level AC excitation current, it does not possess any risks or inconvenience for the patient. The idea of utilizing bioimpedance monitoring of a chronic wound is based on the pathophysiology of the wound. Often the integrity of the skin is lost in chronic wounds, and from an electrical point of view, the loss of high impedance stratum corneum leads into steep decrease in measured impedance. As the healing of the wound proceeds, the wound base lifts up and the wound starts to close up from the peripherals. Finally, the skin integrity is obtained. The gradual gain in the skin integrity is observed as increasing impedance particularly at lower frequencies.

Generally speaking, a chronic wound is trapped in an on-going inflammation phase of the wound healing process. Prolonged inflammation of a chronic wound is characterized by accumulation of highly conductive fluid into the wound and the surrounding area. The fluids may accumulate into the intracellular space as a result of ischemia. If the blood flow to the tissues is interrupted, cell metabolism continues but in an anaerobic way. However, a prolonged ischemia inevitably results in decline of metabolism. This results in the decreased activity of ion pumps, which leads changes in the ion distribution in extracellular fluid and intracellular fluid. The result is cellular edema because of inflow of water and sodium into the cell. The decline of extracellular fluid volume reduces the width of the electrical path of the low frequency current and increases the extracellular resistance. Severe ischemia finally results in cell necrosis. The cellular integrity is lost in necrosis and intracellular fluid leaks into the extracellular space. The necrosis is observed as a decrease in extracellular resistance.

The fluids in a chronic wound may also accumulate into extracellular space. The increased volume of extracellular fluid can be observed as a decrease in the extracellular resistance. Often related to the chronic wounds, the swelling is due to increased vasodilatation and increased permeability of the capillaries. As a result of this the fluid accumulates into the extracellular space. Another possible cause for fluid accumulation is peripheral edema. Peripheral edema results from increased capillary permeability or impaired return of fluid by lymphatic system from the interstitial space to vascular compartment. Lymphedema is a result of impaired function of lymphatic system and the fluid tends to accumulate into the extracellular space.

European patent specification EP 1569553B1 presents a prior art wound mapping system presenting an array of rectangular electrodes that may be used to stimulate wound tissue electrically or measure impedance of wound tissue. The measurement electrodes are isolated from each other by a non-conducting hydrogel layer. In use, the conducting parts of the stimulating electrodes are in direct contact with wound tissue via a hydrogel patch on the exposed conducting electrode. The conducting parts of the stimulating electrodes are designed to be electrically connected to the tissue but not to measure moisture above the wound or at a localised site between the electrodes. However, this allows the electrodes to dry into healing tissue and stick to the healed cell layer. Removal of the device with the wound dressing would remove the healed skin. Application of a hydrogel to the electrodes in contact with the wound area does little to alleviate the problem as it will dry out before removal of the dressing. Development of a tool that would allow objective online monitoring without disturbance would be of great importance.

Conventional prior art wound dressings and prior art electrode arrangements for facilitating wound healing have many problems and disadvantages. Regardless of the massive effort put into and improvements obtained in the area of the treatment of chronic wounds, many chronic wounds still remain non-responsive to the conventional treatment and a need to further develop the existing and new therapeutic methods is obvious. Furthermore, the need for continuous, non-invasive and objective solution for monitoring chronic wound healing without disturbing the delicate healing process is also obvious.

As mentioned above, there are a lot of deficiencies in the current wound dressings and electrode arrangements for facilitating wound healing. There is a clear demand in the market for a new type of an electrode arrangement for facilitating wound healing that would be better and more efficient than the current prior art electrode arrangement solutions. Likewise, there is a clear demand in the market for a new type of a wound dressing having a wound healing electrode arrangement that would be better and more efficient than the current prior art wound dressing solutions.

BRIEF DESCRIPTION OF THE INVENTION

An object of the present invention is thus to provide an electrode arrangement for facilitating wound healing and a wound dressing having an electrode arrangement so as to overcome the above mentioned problems and to alleviate the above mentioned disadvantages.

The objects of the invention are achieved by an arrangement for facilitating wound healing, which arrangement comprises at least two impedance reference electrodes, a frame like counter-electrode and stimulation electrodes in a form of an array; and a bioadhesive affinity layer surrounding the stimulation electrodes; said arrangement being suited for applying on top of the wound so that the stimulation electrode array is on the wound area, and that the at least two impedance reference electrodes and the frame like counter-electrode are suited for placing in contact with the healthy skin surrounding the wound area; which electrodes are suited for applying LIDC type electrical stimulation current to the wound area and for bioimpedance measurement.

Preferably in the arrangement, the frame like counter-electrode is anode electrode and the stimulation electrodes are cathode electrodes, or vice versa. Preferably in the arrangement, the electrodes are suited for bioimpedance measurement with measurement frequencies in the range of 10 Hz-200 000 Hz, preferably in the range of 1 000 Hz-50 000 Hz.

Preferably in the electrode arrangement, the polarity of the frame like counter-electrode and the stimulation electrodes is switchable. Preferably in the electrode arrangement, the electrodes are multiplexed.

Furthermore, the objects of the invention are achieved by a method for measuring wound healing, which method comprises
applying LIDC type electrical stimulation current to the wound area with the help of a frame like counter-electrode and stimulation electrodes in a form of an array, and
performing bioimpedance measurement with the help of said stimulation electrodes;
wherein said electrodes are complemented with at least two impedance reference electrodes suited for placing in contact with the healthy skin surrounding the wound area, and a bioadhesive affinity layer surrounding the stimulation electrodes.

Preferably in the method, the frame like counter-electrode is used as an anode electrode and the stimulation electrodes are used as cathode electrodes, or vice versa. Preferably in the method, the electrodes are suited for bioimpedance measurement with measurement frequencies in the range of 10 Hz-200 000 Hz, preferably in the range of 1 000 Hz-50 000 Hz.

Furthermore, the objects of the invention are achieved by a wound dressing comprising at least two impedance reference electrodes, a frame like counter-electrode and stimulation electrodes in a form of an array; and a bioadhesive affinity layer surrounding the stimulation electrodes; said wound dressing being suited for applying on top of the wound so that the stimulation electrode array is on the wound area, and that the at least two impedance reference electrodes and the frame like counter-electrode are suited for placing in contact with the healthy skin surrounding the wound area; which electrodes are suited for applying LIDC type electrical stimulation current to the wound area and for bioimpedance measurement.

Preferably, the frame like counter-electrode is anode electrode and the stimulation electrodes are cathode electrodes, or vice versa. Preferably, the electrodes are suited for bioimpedance measurement with measurement frequencies in the range of 10 Hz-200 000 Hz, preferably in the range of 1 000 Hz-50 000 Hz.

Preferably, the polarity of the frame like counter-electrode and the stimulation electrodes is switchable. Preferably, the wound dressing has a button battery, a printed battery structure or an electrochemical cell used as a power source for the electrodes.

Preferably, the wound dressing has a tether with the electrical connections of the electrodes. More preferably, the tether has a tether connector connectable to an electrode routing plug of an outside measurement terminal device and/or to an external power source. Preferably, the wound dressing is produced by reel-to-reel print manufacturing, by sheet print manufacturing, by rotary screen print manufacturing or by any other mass production print manufacturing.

Preferably, the electrodes and the conductor pattern are printed to a paper substrate, to a polymer substrate or to a composite substrate functioning as a body of the wound dressing. Alternatively, the electrodes and the conductor pattern are etched on top of a suitable layer of plastic laminate, metal laminate or a composite laminate and the etched laminate layer is attached to a paper substrate, polymer substrate or composite substrate functioning as a body of the wound dressing.

Preferably, the bioadhesive affinity layer is manufactured of a peptide modified polysaccharide bioadhesive comprising a peptide component and a polysaccharide component. More preferably, the peptide component is an integrin binding peptide, such as Arg-Gly-Asp (RGD), Gly-Arg-Gly-Asp-Ser (GRGDS), or cyclic RGD.

Preferably, the polysaccharide component is galactoglucomannan, xyloglucan or galactomannan. Alternatively, the polysaccharide component is spruce galactoglucomannan. Preferably, the polysaccharide component comprises galactose side units. Preferably, surface modification is applied to the wound dressing.

Preferably, the wound dressing comprises a bioactive layer. More preferably, the bioactive layer contains a biopolymer based bioactive glass granules or spheres containing screen printable paste. More preferably, said screen printable paste contains polylactic acid (PLA) as the polymer component and 20-100 µm granules of an antimicrobial angiogenesis-promoting bioactive glass, e.g. BAG-S53P4. Preferably, antibacterial silver is applied to the wound dressing. Preferably, the wound dressing is used for facilitating wound healing.

In the following, the invention will be described in greater detail by means of preferred embodiments with reference to the accompanying drawings of FIGS. 1 to 4.

DETAILED DESCRIPTION OF THE INVENTION

Figure 1:
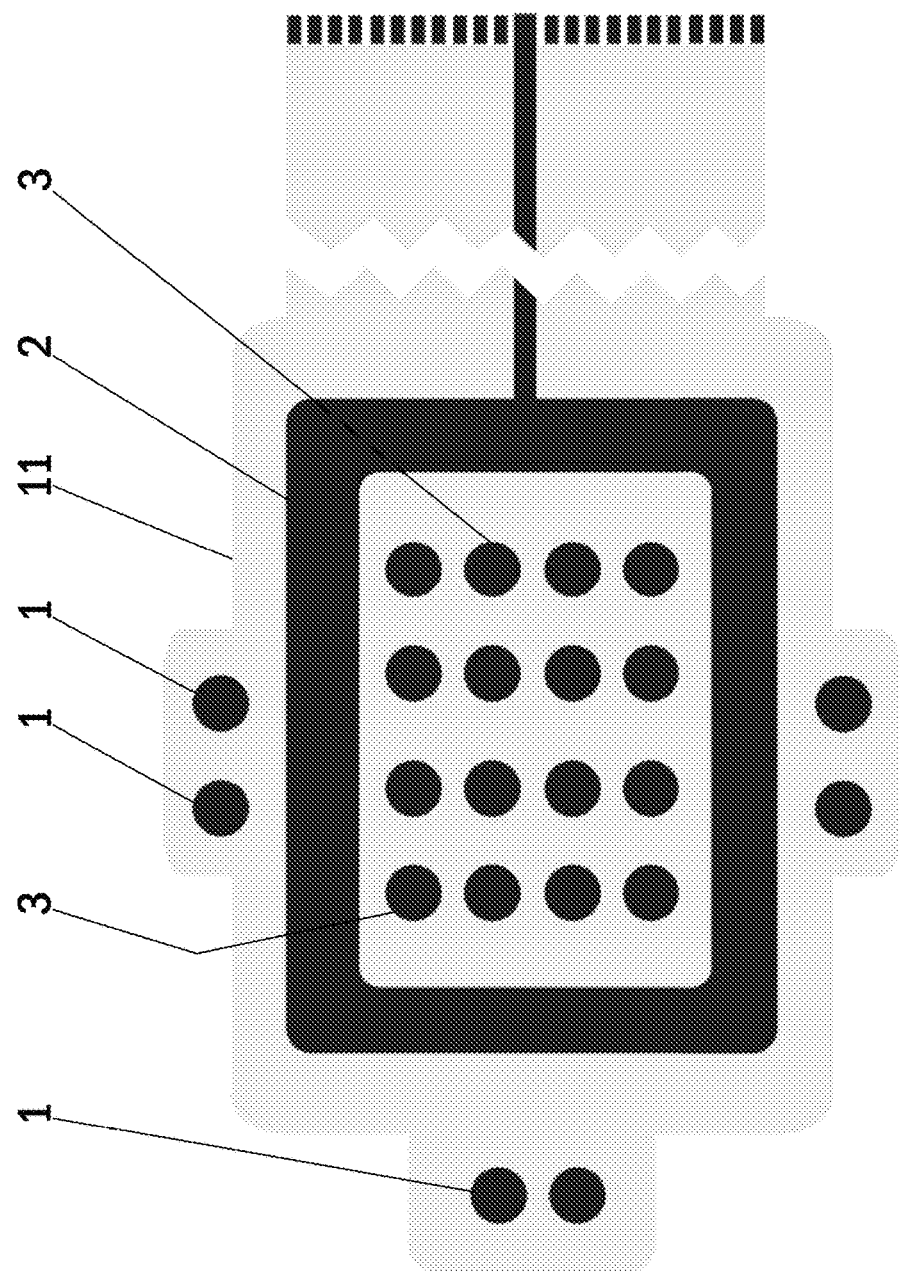
FIG. 1 shows a bottom side view of an electrode arrangement of one embodiment of a wound dressing according to the present invention.

FIG. 1 shows a bottom side view of an electrode arrangement of one embodiment of a wound dressing according to the present invention. The wound dressing according to the present invention comprises a printed substrate 11 having impedance reference electrodes 1, a frame like counter electrode 2 and stimulation electrodes 3 in a form of an array printed on the printed substrate 11. Highly conductive screen printable inks may be used as the material for the electrodes 1-3. The electrodes 1-3 and the conductor pattern may be printed directly to a paper substrate 11, polymer substrate 11 or composite substrate 11 functioning as the wound dressing laminate. Another alternative is to etch the electrodes 1-3 and the conductor pattern on top of a suitable layer of plastic laminate 11, metal laminate 11 or a composite laminate 11 and attach this etched laminate layer 11 to a paper substrate, polymer substrate or composite substrate functioning as the wound dressing laminate. Importantly, this part may be provided in any size and shape.

Figure 2:
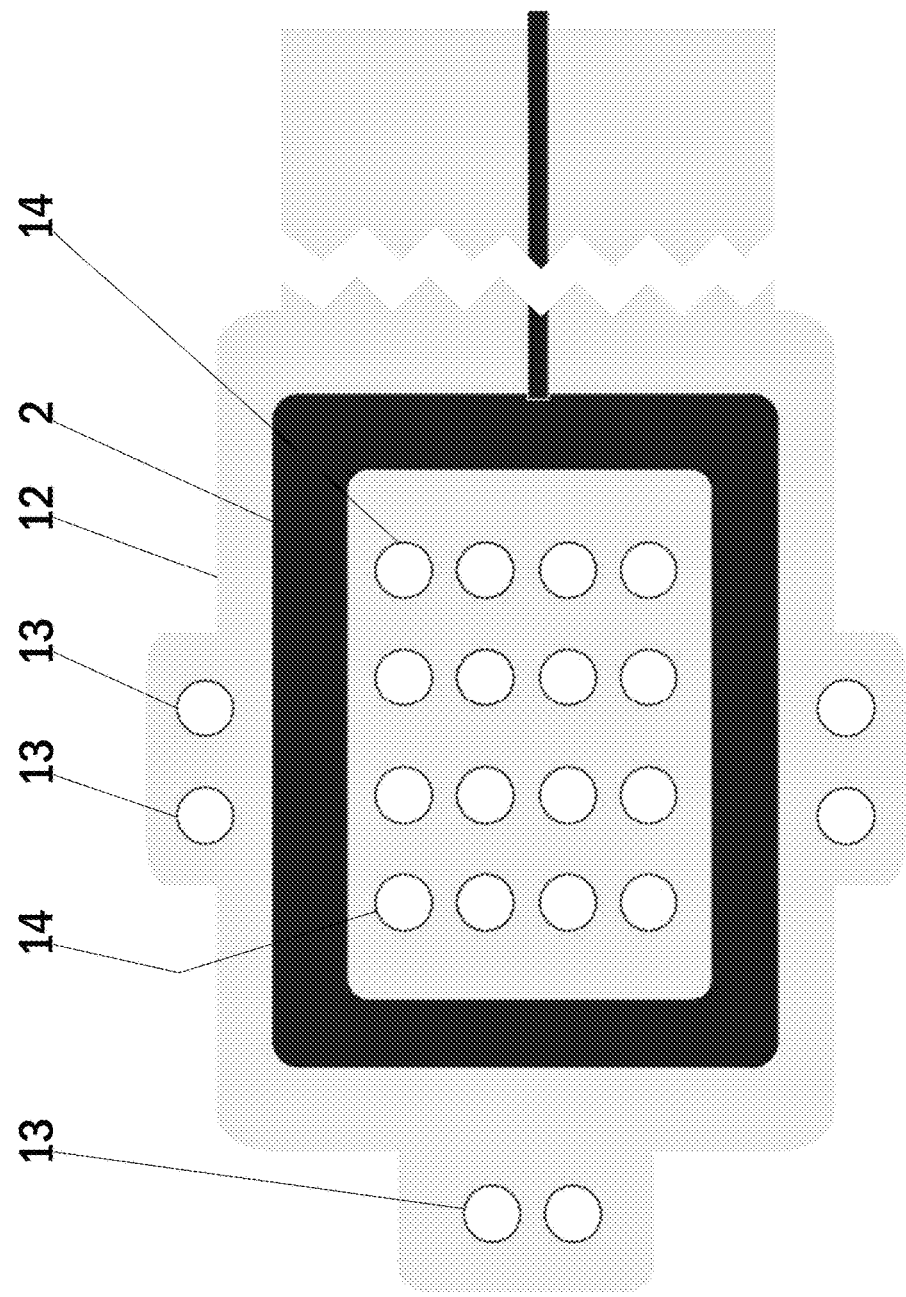
FIG. 2 shows a bottom side view of a lower laminate part of an electrode arrangement of one embodiment of a wound dressing according to the present invention.

FIG. 2 shows a bottom side view of a lower laminate part of an electrode arrangement of one embodiment of a wound dressing according to the present invention. The lower laminate part 12 of an electrode arrangement of a wound dressing according to the present invention contains a printed or etched frame like counter electrode 2 and a number of perforations 13, 14 to allow for wound contact with the stimulation electrode array and impedance reference electrodes. Highly conductive screen printable inks may be used as the material for the frame like electrode 2. The electrode 2 and the conductor pattern may be printed directly to a paper substrate 12, polymer substrate 12 or composite substrate 12 functioning as the lower part of the wound dressing laminate. Another alternative is to etch the electrode 2 and the conductor pattern on top of a suitable layer of plastic laminate 12, metal laminate 12 or a composite laminate 12 and attach this etched laminate layer 12 to a paper substrate, polymer substrate or composite substrate functioning as the lower part of the wound dressing laminate. Importantly, this part may be provided in any size and shape.

Figure 3:
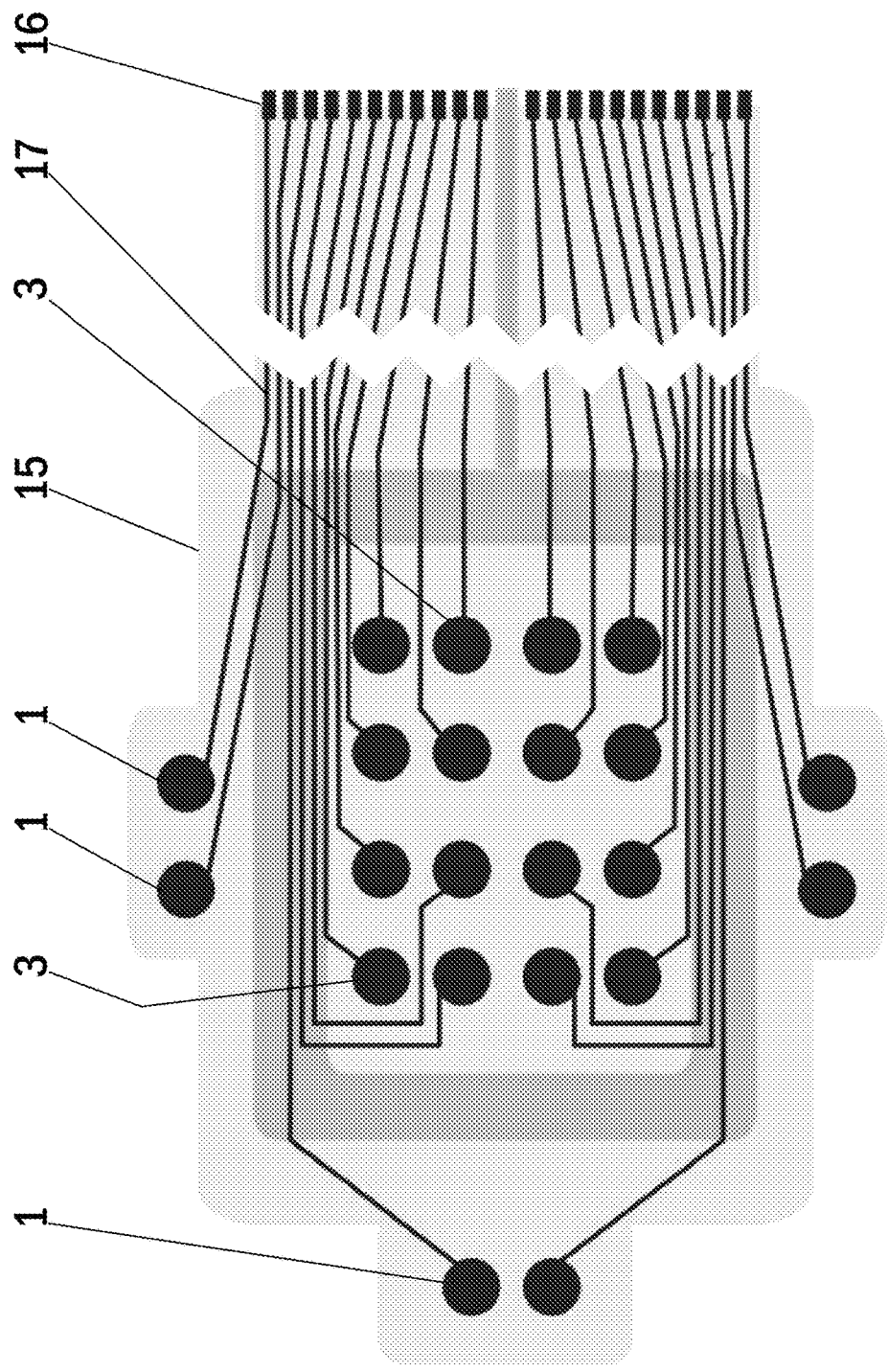
FIG. 3 shows a bottom side view of an upper laminate part of an electrode arrangement of one embodiment of a wound dressing according to the present invention.

FIG. 3 shows a bottom side view of an upper laminate part of an electrode arrangement of one embodiment of a wound dressing according to the present invention. The upper laminate part 15 of an electrode arrangement of a wound dressing according to the present invention contains a printed or etched substrate 15 having impedance reference electrodes 1 and stimulation electrodes 3 in a form of an array printed or etched on the substrate 15. The upper laminate part 15 shown in the FIG. 3 also contains printed connectors 16 and wiring layout 17. Highly conductive screen printable inks may be used as the material for the reference electrodes 1 and the stimulation electrodes 3. The electrodes and the conductor pattern may be printed directly to a paper substrate 15, polymer substrate 15 or composite substrate 15 functioning as a body of the wound dressing.

Another alternative is to etch the electrode array and the conductor pattern on top of a suitable layer of plastic laminate 15, metal laminate 15 or a composite laminate 15 and attach this etched laminate layer 15 to a paper substrate, polymer substrate or composite substrate functioning as the upper part of the wound dressing laminate. The stimulation electrode array 3 may comprise any desired number of electrodes in any desired configuration. A typical non-limiting electrode array comprises 10 to 200 electrodes. The number of arrayed electrodes depends, at least party, from the size and the shape of the wound dressing. Importantly, the wound dressing may be provided in any sizes and shapes.

Figure 4:
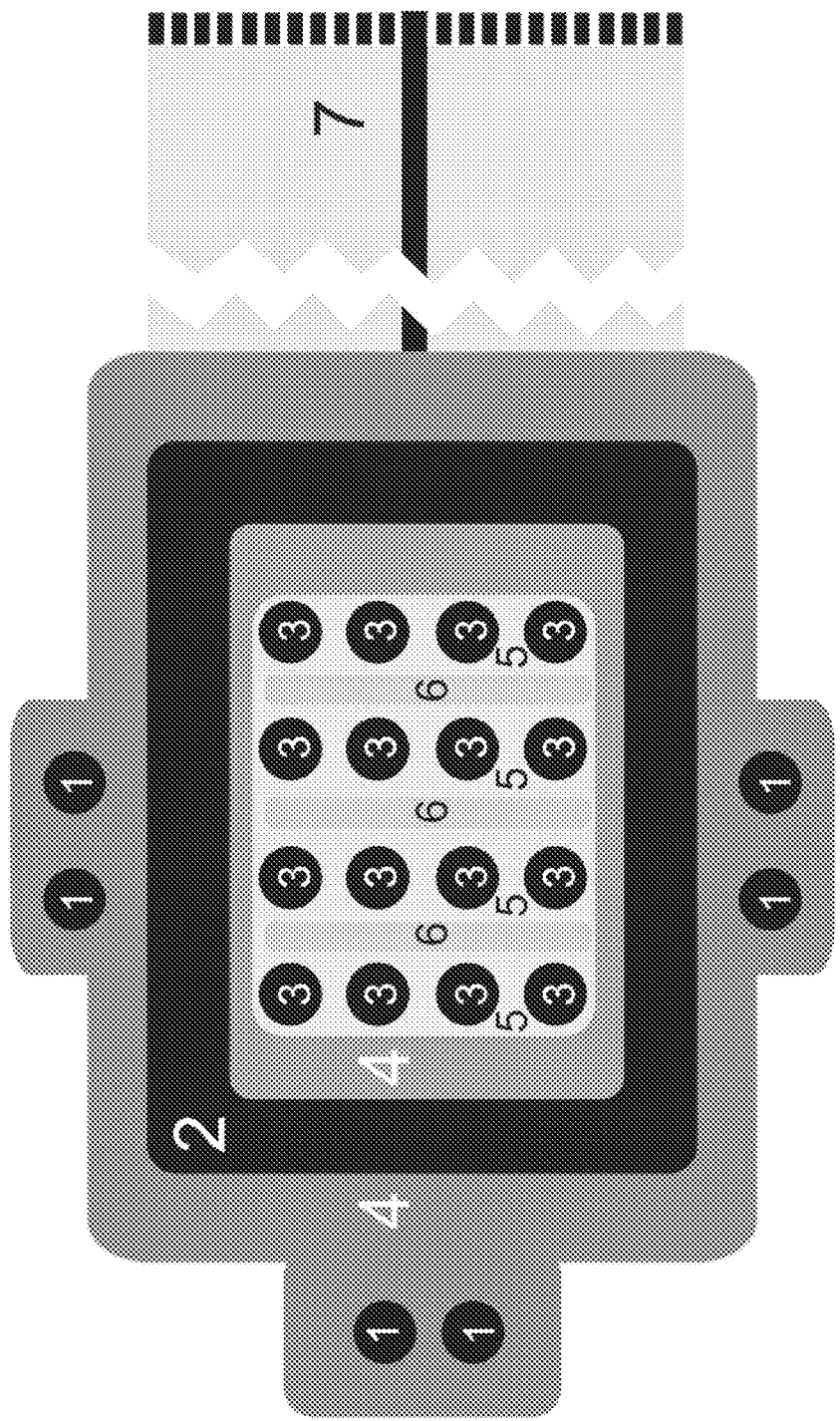
FIG. 4 shows a bottom side view of one embodiment of a wound dressing according to the present invention.

FIG. 4 shows a bottom side view of one embodiment of a wound dressing according to the present invention. The wound dressing according to the present invention contains impedance reference electrodes 1, a frame-like counter electrode 2, a stimulation electrode array 3, a hydrogel adhesive layer 4, a bioadhesive affinity layer 5, a bioactive layer 6 and a tether with a tether connector 7 connectable to an electrode routing plug of an outside measurement terminal device. Impedance reference electrodes 1 provide the reference value for the wound impedance measurement. The frame-like electrode 2 acts as the counter electrode and the stimulation electrode array 3 provides the stimulation current during LIDC stimulation. When mapping the wound various combinations of electrode pairs of the stimulation electrode array 3 can be measured.

When assessing swelling and/or onset of infection the four corner electrodes of the stimulation electrode array 3 can be used. The hydrogel adhesive layer 4 is coated with a suitable non-conductive hydrogel acting as an adhesive. The bioadhesive affinity layer 5 is coated with a peptide modified polysaccharide bioadhesive to be used in the bioadhesive affinity layer 5 and comprises a peptide component and a polysaccharide component. Preferably, the peptide component is an integrin binding peptide, such as Arg-Gly-Asp (RGD), Gly-Arg-Gly-Asp-Ser (GRGDS), or cyclic RGD. The peptide component provides bioadhesive and hemostatic properties to the present wound dressing, at least partly, owing to its ability to enhance endothelial cell adhesion and proliferation. A number of different polysaccharides having high affinity for cellulosic surfaces may be used as the polysaccharide component in the peptide modified polysaccharide bioadhesive to be used in the bioadhesive affinity layer 5. Preferably, the polysaccharide component comprises galactose side units. A non-limiting example of suitable polysaccharide species is galactoglucomannan, the major hemicellulose type or heteropolysaccharide in softwoods. In one particular embodiment, the polysaccharide component is spruce galactoglucomannan. Other non-limiting examples of suitable polysaccharide species include xyloglucan and galactomannan.

The peptide modified polysaccharide bioadhesive may be produced by activation of the galactose side units in the selected polysaccharide through chemo-enzymatic processes in water medium. Next, the peptides are anchored to these activated sites by peptide coupling while maintaining the integrity of the polysaccharide main chain and hence the affinity towards a cellulosic surface of the wound dressing. Alternative materials for the bioadhesive affinity layer 5 include chitosan and derivatives thereof.

The bioactive layer 6 in FIG. 4 contains a biopolymer based bioactive glass granules or spheres containing paste. This screen printable paste may contain polylactic acid (PLA) as the polymer component and 20-100 µm granules of an antimicrobial angiogenesis-promoting bioactive glass, e.g. BAG-S53P4. The electrode routing plug may be integrated directly to the measurement device, or a communication tether may be used in between. The length of the tether of the wound dressing according to the present invention may be very short (in the range of centimeters) or very long (in the range of meters) or something in between. As a power source for the wound dressing according to the present invention a button battery or a printed battery structure, realized either as a hybrid (zinc/air or aluminium/air) or as fully chemical (zinc/silver oxide) battery may be used. Also an electrochemical cell e.g. using enzyme catalyst may be used as a power source for the wound dressing according to the present invention. One such electrochemical cell using enzyme catalyst has been described in an International patent application WO 2007/147942. Hence, the tether connector is providing contact to the power supply containing connector during stimulation and to the bioimpedance measuring device during evaluation of degree of wound healing.

The principal idea of application of the wound dressing according to the present invention is that the wound dressing is applied on top of the wound so that the stimulation electrode array 3 is on the wound area and the frame like counter-electrode 2 is on and in contact with the intact skin surrounding the wound area. The frame like counter-electrode 2 may e.g. be square formed. The stimulation electrode array 3 may e.g. be a simulation software optimized stimulation electrode array 3.

The injured tissue is normally characterized by a higher potential compared with the surrounding intact skin and in the wound edge cells are in electric field. Electrical stimulation according to the present invention restarts or accelerates wound healing process by imitating the natural electrical current and to increase this lateral current, positive polarity should be placed on the wound and negative on the intact skin area. The polarity of the wound may also be reversible. When applying electrical stimulation to the wound the current density should be sufficiently high in the wound and the electrode layout should be selected such that the current reaches the deeper skin layers. As electrical stimulation is applied to the wound there is regenerated epithelium and granulation tissue being formed under the wound stimulation points this will increase the local contact resistance between the stimulation electrode and the wound. This causes the stimulation current to seek to wound stimulation points where the healing is slower this resulting to a more even stimulation effect. Thus, the present wound dressing may be termed as self-adjustable.

In the wound dressing according to the present invention point-like stimulation electrodes of the stimulation electrode array 3 on the wound surface provide a better skin contact to the wound when compared to larger structures due to more flexible surface of the wound dressing. The electrode placement according to the present invention also provides better current density feature and additionally gives possibility to self-regulatory adjustment of the wound stimulation current as the impedance increases at the edges of the wound as the healing proceeds and the stimulation current naturally seeks lower impedance pathway. This electrode placement also offers a possibility to polarity reversal. The polarity of the frame like counter-electrode 2 and the stimulation electrodes 3 is switchable during treatment to enhance the diffusion of various wound healing related components and decrease the formation of concentration gradients. The electrodes 2, 3 can also be multiplexed so as to allow for measurement of bioimpedance in a two electrode and four electrode configurations.

The wound dressing structure according to the present invention is flexible and thin and the wound dressing surface area is scalable. The proposed wound dressing is self-sustaining and does not involve leads during stimulation functionality, thereby providing overall convenience and ease of use for the patient. The wound dressing structure according to the present invention may be manufactured by using reel-to-reel print manufacturing. At least the electrodes and potentially an integrated power source in the wound dressing may be produced by reel-to-reel print manufacturing. Also a surface modification may be applied to the wound dressing in order to enhance the wound contact for example by drop casting, by curtain spraying or by administration of skin adhesive using spraying techniques.

In some embodiments, antibacterial silver may be used in the wound dressing surface facing the wound; this improving the antimicrobial properties against wound infection. Furthermore, bioactive glass may be used in the wound dressing surface facing the wound as bioactive glass possesses good antimicrobial properties. The use of bioactive glass may provide additional protection against wound infection or reduce the on-going infection. Moreover, bioactive glasses enhance angiogenesis, or blood vessel growth, a process that is critical in wound healing. Suitable bioactive glasses are readily available and easily chosen by a person skilled in the art.

One of the signs of a wound infection is an increase in body temperature around the wound area. Thus, if desired, a built-in thermometer or thermocouple can be included in the present wound dressing to allow early detection and monitoring of a possible wound infection.

The wound dressing according to the present invention incorporates galvanic wound stimulation functions with a wound healing monitoring possibility by using bioimpedance method. The measurement of bioimpedance is non-intrusive and do not require removal of the wound dressing, therefore it may be used in less controlled environment such as in home care.

The bioimpedance monitoring of wound healing is based on the impedance measurement of wound tissue in reference to intact skin. Three most common electrode systems include 2-, 3- and 4-electrode systems. In one embodiment of the present invention the wound healing monitoring is performed by utilizing 2-electrode bioimpedance measurement configuration. In the 2-electrode bioimpedance measurement configuration the same electrodes are used for both the excitation current feeding and voltage measurement. The output of 2-electrode bioimpedance measurement consists of the electrode impedance of both electrodes, the skin impedance under both electrodes and the tissue impedance between the two measurement electrodes. The outer layers of skin provide very high impedance compared to underlying tissues. Therefore, the strongest indication of wound healing can be obtained when the impedance of various skin layers is included in the measurements. The 2-electrode bioimpedance measurement method outputs so called true impedance since negative sensitivity areas do not exist in this configuration. This makes the analysis of the measurement results less prone to misinterpretations.

Skin impedance can also be measured using the 3-electrode bioimpedance measurement configuration; however this includes certain obvious disadvantages. The 3-electrode bioimpedance measurement includes areas of negative sensitivity, which may compromise correct interpretation of the output. Placing of the third electrode is important for obtaining reliable and comparable results; this may also prove to be difficult and impractical in clinical use.

With the help of this structure the wound dressing according to the present invention may generate and repair the bio-mimicking potential difference between the wound area and the surrounding intact skin. The wound dressing according to the present invention may deliver a micro-amperage DC stimulus current to the wound tissue. The wound dressing according to the present invention may be used alongside with the conventional wound care practices. The stimulus current may be limited by either separately printed resistors, internal resistance of the battery or possibly only by the skin/tissue impedance, so that the treatment current is self-regulated. The stimulus current may be fed to the wound surface through multiple antibacterial silver pathways; this improving the electrode-skin contact.

A wound healing process usually starts from the edges of the wound and the wound base lifts up. The skin integrity is gradually regained and the amount of exudates is reduced in the peripheral wound area. Consequently, the impedance increases, and more current flows to the open and moist centre of the wound which provides a lower impedance pathway. In the use of the wound dressing according to the present invention the stimulation current penetrates the skin surface and enters to the underlying wound tissue, thus improving the healing impact.

The bioimpedance measurements may be carried out using at least one frequency depending on the width and the depth of the wound. Measurement frequencies in the range of 10 Hz-200 000 Hz and preferably in the range of 1 000 Hz-50 000 Hz may be used. The bioimpedance measurement of the wound dressing according to the present invention may be based on a stand-alone-device and connected to the wound dressing 12 only for the time of measurement.

Due to the electrical simplicity of the wound dressing, a communication tether is to be used between the outside measurement terminal device and the wound dressing. The tether provides galvanic connection between the outside measurement terminal device and the impedance measurement electrodes on the wound dressing. In a certain embodiment, the patch may contain intelligent electronics, and a wireless communication method, such as e.g. infrared communication method or RF communication method may provide the connection to the measurement device instead.

The impedance measurement device may be a handheld device. The impedance measurement device may have a flat connector probe that is slid into a fold on the patch. Alternatively, the impedance measurement device may have a measurement clip that clamps around a contact extrusion on the patch. Furthermore alternatively, the impedance measurement device may be pressed against contacts on the patch.

In addition to the impedance measurement functionality the outside measurement terminal device may contain means to display the result immediately to the operator, store the measured data and to upload the data to the operator's personal computer. As the device may be used in clinical trials, precautions will be taken to make the electrical and physical interfaces of the device safe.

Monitoring the wound healing process through bioimpedance measurements is very precise and sensitive. Even wounds as small as a puncture wound made by a needle are detectable and monitorable by the present arrangement. The same applies to wound types the healing which is particularly challenging to be monitored otherwise, i.e. wounds excreting pus or other fluids.

The present wound dressing may be used to treat any type of wounds, in particular chronic wounds. As used herein, the term "treatment" refers not only to a complete healing of a wound, but also to alleviation and amelioration of symptoms related to incomplete or improper wound healing, including, but not limited to, pain, swelling or edema, burning, itching, rash, redness, discoloration and dry, scaly skin.

Chronic wounds, or ulcers, are wounds or open sores that will not heal or keep returning. Ulcers may develop anywhere on a human body, foot and leg ulcers being the most typical ulcer types. Non-limiting examples of ulcers to be treated in accordance with the present invention include pressure ulcers, or bedsores, venous ulcers, neuropathic (diabetic) ulcers, and arterial (ischemic) ulcers. Typically in foot and leg ulcers, the present wound dressing is to be worn under compression stockings.

Also burn wounds, including first to third degree burns, may be treated with the wound dressing according to the present invention. As the present wound dressing is fully scalable, it may in some extreme embodiments be formulated as a bed sheet to cover large-surface wounds, such as large-surface burn wounds.

The wound dressing according to the present invention and the electrode arrangement for facilitating wound healing according to the present invention provide clear advantages and improvements in the area of the treatment of chronic wounds. The wound dressing according to the present invention and the electrode arrangement for facilitating wound healing according to the present invention provide a continuous, non-invasive and objective solution for monitoring chronic wound healing without disturbing the delicate healing process.

A further important advantage of the present wound dressing and the electrode arrangement for facilitating wound healing is easy hygienic disposal with hospital or household waste. This is made possible by using only combustible and/or biodegradable materials in the wound dressing and the electrode arrangement.

It will be obvious to a person skilled in the art that, as the technology advances, the inventive concept can be implemented in various ways. The invention and its embodiments are not limited to the examples described above but may vary within the scope of the claims.

The invention claimed is:

1. An arrangement for facilitating wound healing, said arrangement capable of being applied on top of a wound and comprising:
    at least two impedance reference electrodes and a frame like counter-electrode which are capable of being placed in contact with healthy skin surrounding a wound area,
    stimulation electrodes in a form of an array capable of being placed on the wounded area; wherein the frame like counter-electrode is outside the array and formed such that the frame like counter-electrode extends contiguously parallel to stimulation electrodes at adjacent sides of the array, and
    a bioadhesive affinity layer surrounding the stimulation electrodes; and
    wherein the frame like counter-electrode and the stimulation electrodes are suited for applying low intensity direct current (LIDC) type electrical stimulation current to the wound area and for bioimpedance measurement.

2. The arrangement according to claim 1, wherein the frame like counter-electrode is an anode electrode and the stimulation electrodes are cathode electrodes, or vice versa.

3. The arrangement according to claim 1, wherein the electrodes are suited for bioimpedance measurement with measurement frequencies in the range of 10 Hz-200 000 Hz.

4. The arrangement according to claim 1, wherein the polarity of the frame like counter-electrode and the stimulation electrodes is switchable.

5. The arrangement according to claim 1, wherein the electrodes are multiplexed.

6. A method for measuring wound healing, comprising:
    applying low intensity direct current (LIDC) type electrical stimulation current to a wound area with the help of a frame like counter-electrode and stimulation electrodes in a form of an array, wherein the frame like counter-electrode is outside the array and formed such that the frame like counter-electrode extends parallel to stimulation electrodes at adjacent sides of the array, and
    performing bioimpedance measurement with the help of said stimulation electrodes;
    wherein said frame like counter-electrode and the stimulation electrodes are complemented with at least two impedance reference electrodes suited for placing in contact with healthy skin surrounding the wound area, and a bioadhesive affinity layer surrounding the stimulation electrodes and wherein the frame like counter electrode extends contiguously around the corner of adjacent sides of the array.

7. The method according to claim 6, wherein the frame like counter-electrode is used as an anode electrode and the stimulation electrodes are used as cathode electrodes, or vice versa.

8. The method according to claim 6, wherein the electrodes are suited for bioimpedance measurement with measurement frequencies in the range of 10 Hz-200 000 Hz.

9. A wound dressing, comprising:
- at least two impedance reference electrodes, a frame like counter-electrode and stimulation electrodes in a form of an array, wherein the frame like counter-electrode is outside the array and formed such that the frame like counter-electrode extends parallel to stimulation electrodes at adjacent sides of the array; and
- a bioadhesive affinity layer surrounding the stimulation electrodes;

wherein said wound dressing is suited for applying on top of a wound so that the stimulation electrodes are on the wound area, and that the at least two impedance reference electrodes and the frame like counter-electrode are suited for placing in contact with healthy skin surrounding the wound area; and the electrodes are suited for applying low intensity direct current (LIDC) type electrical stimulation current to the wound area and for bioimpedance measurement,
wherein the frame like counter-electrode extends parallel and in a single section to simulation electrodes at adjacent sides of the array.

10. The wound dressing according to claim 9, wherein the frame like counter-electrode is an anode electrode and the stimulation electrodes are cathode electrodes, or vice versa.

11. The wound dressing according to claim 9, wherein the electrodes are suited for bioimpedance measurement with measurement frequencies in the range of 10 Hz-200 000 Hz.

12. The wound dressing according to claim 9, wherein the polarity of the frame like counter-electrode and the stimulation electrodes is switchable.

13. The wound dressing according to claim 9, wherein the wound dressing has a button battery, a printed battery structure or an electrochemical cell used as a power source for the electrodes.

14. The wound dressing according to claim 9, wherein the wound dressing has a tether with electrical connections of the electrodes.

15. The wound dressing according to claim 14, wherein the tether has a tether connector connectable to an electrode routing plug of an outside measurement terminal device and/or to an external power source.

16. The wound dressing according to claim 9, wherein the electrodes and a conductor pattern are etched on top of a suitable layer of plastic laminate, metal laminate or a composite laminate, and the etched laminate layer is attached to a paper substrate, polymer substrate or composite substrate functioning as a body of the wound dressing.

17. The wound dressing according to claim 9, wherein the bioadhesive affinity layer is manufactured of a peptide modified polysaccharide bioadhesive comprising a peptide component and a polysaccharide component.

18. The wound dressing according to claim 9, wherein the wound dressing comprises a bioactive layer.

19. The wound dressing according to claim 18, wherein the bioactive layer contains a biopolymer based bioactive glass granules or spheres containing screen printable paste.

20. The wound dressing according to claim 19, wherein said screen printable paste contains polylactic acid (PLA) as the polymer component and 20-100 μm granules of an antimicrobial angiogenesis-promoting bioactive glass.

\* \* \* \* \*